United States Patent [19]

Miller

[11] Patent Number: 4,520,111
[45] Date of Patent: May 28, 1985

[54] DIAGNOSTIC METHOD FOR DETERMINING CONTENT OF SIALIC ACID OR SIALOPROTEIN

[75] Inventor: Ronald L. Miller, Charleston, S.C.

[73] Assignee: Research Corporation, New York, N.Y.

[21] Appl. No.: 574,235

[22] Filed: Jan. 26, 1984

Related U.S. Application Data

[62] Division of Ser. No. 355,378, Mar. 8, 1982, Pat. No. 4,457,865.

[51] Int. Cl.³ .................... G01N 1/00; G01N 33/48; C07G 7/00
[52] U.S. Cl. .................... 436/501; 260/112 R; 436/63; 436/64; 436/71; 436/74; 436/502; 436/520; 436/813; 436/827
[58] Field of Search ............ 260/112 R; 436/71, 501, 436/502, 520, 813, 63, 64, 74, 827

[56] References Cited

U.S. PATENT DOCUMENTS 4,115,062 9/1978 Morre et al. .................... 436/71 X

OTHER PUBLICATIONS

Allan et al., Nature (London) New Biol., 236, 123–125, (1972).
Hayman et al., Febs. Letters, 29, 185–188, (1973).
Lotan et al., Biochemistry, 16, 1787–1792, (1977).
Bhavanandan et al., J. Biol. Chem., 254, 4000–4008, (1979).
Dorai et al., Anal. Biochem., 115, 130–137, (1981).
Pearlstein, Exp. Cell. Res. 109, 95–103, (1977).
Dawson et al., J. Immunol. 1190–1193, (1974).
Baenziger et al., J. Biol. Chem., 254, 2400–2407, (1979).
Reisner et al., Trends in Biochemical Sciences, vol. 5, 29–31, (1980).
Miller et al., Abstract, FASEB Meeting, May 31–Jun. 4, 1981, St. Louis, MO.
Smith et al., Biochemistry, 12, 2111–2118, (1973).
Arch. Biochem. Biophys. 209, 325–333, (1981), Dorai et al.
Pemberton, Vox Sang. vol. 18, pp. 74–76, (1970).

Primary Examiner—Howard E. Schain
Attorney, Agent, or Firm—Scully, Scott, Murphy & Presser

[57] ABSTRACT

A hemagglutinate lectin derived from the slug, *Limax flavus,* having a high degree of hemagglutinative inhibitory specificity and selectivity for sialic acid or sialoproteins and diagnostic and separatory methods and compositions based upon the inhibitory effect of sialoproteins or sialic acid on the hemagglutinating properties of the slug-derived lectin.

6 Claims, 7 Drawing Figures

DIAGNOSTIC METHOD FOR DETERMINING CONTENT OF SIALIC ACID OR SIALOPROTEIN

This is a divisional of co-pending application Ser. No. 355,378 filed Mar. 8, 1982 now U.S. Pat. No. 4,457,865.

BACKGROUND OF THE INVENTION

It has been well documented in the art that many diverse biological functions are associated with the presence of sialoglycoproteins and sialoglycolipids at or near the cell surfaces in mammals. It has been shown, for example, that the metastasis of malignant cells may be a direct function of an excessive release by the malignant cells, or by other cells, of sialoproteins or sialopeptides into the blood stream. The following is a list of representative literature references documenting the correlation between various biological functions and the presence of at or near the cell surface or the release from the cell of sialopeptides or sialoproteins: Gandhi et al, Effect of Diabetes Mellitus on Sialic Acid and Glutathione Content of Human Erythrocytes of Different Ages, *Indian Journal of Experimental Biology*, Vol. 17, pp. 585-587 (June, 1979); Wautier et al, A Platelet Defect in a Patient with Eosinophilic Leukaemia: Ristocetin-Induced Platelet Aggregation Associated with a Reduced Platelet Sialic Acid Content, *Scand. J. Haematol.*, Vol. 22, pp. 267-276 (1979); Sato et al, Target of X Irradiation and Dislocation of Sialic Acid in Decrease of Cell Surface Charge of Erythrocytes, *Radiation Research*, Vol. 69, pp. 367-374 (1977); Buck et al, Sialoglycoprotein Differences Between Xenotransplantable and Nonxenotransplantable Ascites Sublines of the 13762 Rat Mammary Adenocarcinoma, *Archives of Biochemistry and Biophysics*, Vol. 198, pp. 12-21 (1979); Dawson et al, Variations in Sialomucins in the Mucosa of the Large Intestine In Malignancy: A Quantative and Statistical Analysis, *Biochemical Journal*, Vol. 10, p. 559 (1978); Hakim, Correlation Between Perchloric-Acid-Soluble Serum Proteins, Cellular Immunity and Tumor-Cell Burden, *Int. J. Cancer*, Vol. 25, pp. 281-288 (1981); Hassing et al, Ultraviolet Difference Spectral Studies on Concanavalin A-Carbohydrate Interaction, *Eur. J. Biochem.* Vol. 16, pp. 549-556 (1970); Lipton et al, Glycoproteins and Human Cancer, *Cancer*, Vol. 43, pp. 1766-1771 (1979); Gorman et al, Determination of Protein-Ligand Equilibria by Difference Spectroscopy. Hemerythrin-Ligand Thermodynamic Studies, *Biochemistry*, Vol. 20, pp. 38-43 (1981); Moss et al, Significance of Protein-Bound Neuraminic Acid Levels in Patients with Protein-Bound Neuraminic Acid Levels in Patients with Prostatic and Bladder Carcinoma, *Urology*, Vol. 13, p. 182 (1979); Codington et al, Variations in the Sialic Acid Compositions in Glycoproteins of Mouse Ascites Tumor Cell Surfaces, *Biochemistry*, Vol. 18, pp. 2145-2149 (1979); Sherblom et al, Purification of the Major Sialoglycoproteins of 13762 MAT-B1 and MAT-C1 Rat Ascites Mammary Adenocarcinoma Cells by Density Gradient Centrifugation in Cesium Chloride and Guanidine Hydrochloride, *The Journal of Biological Chemistry*, Vol. 255, pp. 783-790 (1980); Jumblatt et al, Altered Surface Glycoproteins in Melanoma Cell Variants With Reduced Metastasizing Capacity Selected for Resistance to Wheat Germ Agglutinin, *Biochemical and Biophysical Research Communications*, Vol. 95, pp. 111-117 (1980); Vilarem et al, Differences in Sialic Acid Contents of Low Cancer Cells, High Cancer Cells and Normal Mouse Lung Counterparts, *Biochemical and Biophysical Research Communications*, Vol. 98, pp. 7-14 (1981); Gaffar et al, Further Studies on a Human Lung Tumor-associated Antigen, *The Journal of Biological Chemistry*, Vol. 254, pp. 2097-2102 (1979); Blithe et al, Comparison of Glycopeptides from Control and Virus-Transformed Baby Hamster Kidney Fibroblasts, *Biochemistry*, Vol. 19, pp. 3386-3395 (1980); Santer et al, Partial Structure of a Membrane Glycopeptide from Virus-Transformed Hamster Cells, *Biochemistry*, Vol. 18, pp. 2533-2540 (1979); Yogeeswaran et al, Cell Surface Sialic Acid Expression of Lectin-Resistant Variant Clones of B16 Melanoma With Altered Metastasizing Potential, *Biochemical and Biophysical Research Communications*, Vol. 95, pp. 1452-1460 (1980); Glick, Membrane Glycopeptides from Virus-Transformed Hamster Fibroblasts and the Normal Counterpart, *Biochemistry*, Vol. 18, p. 2525 (1979); Allen et al, Glycoprotein Receptors for Concanavalin A Isolated from Pig Lymphocyte Plasma Membrane by Affinity Chromatography in Sodium Deoxycholate; Nature *New Biology*, Vol. 236, pp. 23-25 (1972); Hayman et al, Purification of Virus Glycoproteins by Affinity Chromatography Using Lens Culinaris Phytohaemagglutin, *Febs, Letters.* Vol. 29, pp. 185-188 (1973) Lotan et al, Activities of Lectin and Their Immobolized Derivatives in Detergernt Solutions. Implications on the Use of Lectin Affinity Chromatography for the Purification of Membrane Glycoproteins, *Biochemistry*, Vol. 16, pp. 1787-1794 (1977).

Lectins are a group of proteins that often demonstrate high binding specificity toward carbohydrate residues of glycoproteins and glycolipids. They have proven invaluable in the study of glycoproteins of cell surfaces as well as the modifications they undergo during cell differentiation and malignant transformation. Relatively few lectins with specificity for sialic acid have been identified. Two such lectins, limulin and carcinoscorpin, have been purified from the American horseshoe crab, *Limulus polyphemus*, and the Indian horseshoe crab, *Carcinoscorpius rotunda cauda*, respectively. Limulin also binds N-acetylglucosamine and D-glucuronic acid. The carbohydrate specificity of carcinoscorpin has not been extensively studied. A lectin, LAg-1, which binds N-acetylneuraminic acid, N-glycoylneuraminic acid and N-acetylmannosamine has been isolated from the lobster, *Homarus americanus*. A lectin which binds sialic acid residues of glycoproteins has also been isolated from wheat germ. Agglutination of erythrocytes by wheat germ agglutinin is inhibited by N-acetyl-D-galactosamine and N-acetylneuraminic acid, with N-acetyl-D-glucosamine being the more potent inhibitor.

It has been reported that extracts of the slug, *Limax flavus*, agglutinate red blood cells (Pemberton, *Vox Sang.*, Vol. 18, ppl 74-76 (1970); however, no carbohydrate specificity was defined for the agglutinin.

The specific sialoprotein binding lectin (limulin and carcinoscorpin) of the prior art are relatively unstable, however, due to their large molecular size and multisubunit composition (18 to 20). Moreover, due to the scarcity of the sources for the lectins, the latter are expensive to prepare or procure.

It is an object of the present invention to provide a highly specific sialic acid binding lectin.

It is a further object of the present invention to provide methods for obtaining homogeneous preparations of this lectin from the slugs, *Limax flavus*.

It is a further object of the present invention to provide methods for quantitating the amount of sialoproteins or sialopeptides present in biological fluids or cellular membranes.

It is a further object of the present invention to provide and/or describe methods for the separation and comparison of the sialoproteins and sialopeptides present in biological fluids or solubilized membrane proteins.

It is a further object of the present invention to provide methods for the purification of sialoproteins and sialopeptides in quantities sufficient for antibody preparation to said sialoproteins or sialopeptides.

SUMMARY OF THE INVENTION

The present invention is predicated on the discovery that a lectin isolated from the slug, Limax flavus, has a high degree of specificity and selectivity for binding sialic acid of sialoproteins and sialopeptides. The lectin has a high degree of hemagglutinative activity which is selectively inhibited by sialic acid or sialoproteins.

This hemagglutinating activity of the slug-derived lectin which is selectively inhibited by sialic acid or sialoproteins as opposed to other carbohydrates normally present in mammal biological liquids enables the provision of compositions and diagnostic methods for determining the amount of sialopeptides or sialoproteins present in a biological liquid.

The affinity of the lectin for the sialic acids or sialoproteins also enables the provision of a method for separating sialopeptides residues or sialoproteins from their admixtures with other carbohydrates and proteins.

DETAILED DESCRIPTION OF THE INVENTION

The following definitions apply with respect to the terms used herein and in the appended claims:

"Slug"—the slug, Limax flavus.

"Sialic acid"—the generic name for the family of the N- and O-substituted derivatives of neuraminic acid, e.g., N-acetylneuraminic acid, N-glycolyneuraminic acid and other analogous N- or O-acylated derivatives of neuraminic acid.

"Sialoproteins"—any of the glycoproteins found in mammals containing sialic acid residues.

"Sialopeptides"—any sialic acid containing peptide derived from sialoproteins by cleavage with proteases or by other means.

"Lectin" or "agglutinin"—refers to a group of proteins which bind more or less specifically to carbohydrate residues or glycoproteins.

"LFA"—refers to the sialic acid specific lectin or agglutinin of the slug, Limax flavus.

"Hemagglutinating inhibitory specificity and selectivity for sialic acid or sialoproteins"—refers to the inhibitory effect of sialic acid and sialoproteins on the hemagglutinating properties of the slug-derived lectin as opposed to the relative lack of inhibitory effect of other carbohydrates normally found in mammals on the hemagglutinating activity thereof.

"Ammonium sulfate fractionation"—refers to the conventional method for fractionating proteins from biological liquids based upon the relative insolubility of various protein fractions in ammonium sulfate solutions of varying concentration. (See A. A. Green and W. L. Hughes, Methods in Enzymology (1955) Vol. 1, pp. 32–56, ed. by S. P. Colowick and N. O. Kaplan.)

"Biological liquid or fluid"—refers to any liquid or suspension derived from a mammal, e.g., blood, plasma, serum, urine, tissue homogenate, etc.

"Lectin-sialic acid" or "lectin-sialoprotein complex"—refers to the complex or conjugate formed by the specific binding of the sialic acid or sialic acid residue of the sialoprotein to the slug-derived lectin.

The sialic acid or sialoprotein specific lectin of the present invention is derived from the slug, Limax flavus, by homogenization of the slug tissue to release the lectin from the slug tissues with which it is associated and is partially purified by ammonium sulfate fractionation.

Following the ammonium sulfate fractionation, the lectin fraction may be further purified to homogeneity by affinity chromatography on a sialic acid containing protein bound to an inert substrate such as sepharose, etc. to yield a homogeneous slug lectin preparation having the approximate amino acid composition:

| Amino Acid | Moles per 22,000 g of lectin (Nearest Integer) |
| --- | --- |
| Asx (asparagine + aspartic acid) | 26 |
| Thr | 13 |
| Ser | 13 |
| Glx (glutamine & glutamic acid) | 14 |
| Pro | 4 |
| Gly | 22 |
| Ala | 16 |
| Val | 7 |
| Met | 2 |
| Ile | 7 |
| Leu | 15 |
| Tyr | 10 |
| Phe | 10 |
| His | 7 |
| Lys | 17 |
| Trp | 6 |
| Arg | 8 |
| Cys | 6 |

It will be understood by those skilled in the art that the approximate amino acid composition set forth herein above is accurate to within about ±10% with respect to the various amino acid contents set forth.

The high specificity and selectivity of the slug derived lectin for sialic acid and sialoproteins enables its use as an agent for separating or isolating sialoproteins or sialopeptides from other proteins or peptides and glycoproteins in biological liquids or other solutions or suspensions. The present invention provides a method for isolating sialopeptides or sialoproteins from a biological or non-biological liquid comprising contacting the liquid with the above described lectin to form a lectin-sialopeptide or lectin-sialoprotein complex from the liquid by, e.g., centrifugation to collect the lectin-sialoprotein or lectin-sialopeptide precipitate. The amount of protein in the precipitate can be quantitated by analyzing the precipitate for protein content by any of several commonly used procedures such as the Lowry, Nesseler or the Coomassie blue procedure of BioRad. The amount of sialoproteins and/or sialopeptides present in biological fluids can also be determined by determining the ability of the fluids to inhibit the interaction of a labeled sialoprotein or sialopeptide with the lectin in radioimmunoassays or Elisa type assays. Alternatively, the sialoproteins or sialopeptides present in the precipitate can be solubilized in a sodium dodecyl sulfate and β-mercaptoethanol containing buffer and separated by the sodium dodecyl sulfate-polyacrylamide gel method of Laemmli (Laemmli, U.K., Nature (London) Vol. 227, pp. 680–685, 1970). The sialoproteins or sialopeptides are separated according to size and can be visualized on the gel by staining the protein bands with protein or carbohydrate specific stains such as Coomassie blue or periodic acid Schiff's base staining procedures. In this way the sialoproteins or sialopeptide composition of various biological sources can be compared directly.

A preferred method of separation of sialoproteins or sialopeptides, in quantities sufficient for characterization, from biological liquids involves affinity chromatographic techniques whereby the slug-derived lectin is bound to an insoluble matrix, such as sepharose, Sephadex or polyacrylamide, inert to the biological liquid and suitable for affinity chromatography and contacting the biological liquid therewith in an affinity chromatographic column. The lectin can be coupled to an insoluble matrix by any of a number of published procedures. One convenient method is to couple the slug lectin to Sepharose 4B according to the procedure of Marsh et al (March, S. C., Parikh, 11, and Cuatrecasas, P., *Anal. Biochem.*, Vol. 60, pp. 149–152, 1973), whereby cyanogen bromide is used to activate Sepharose 4B with subsequent interaction of the lectin with the activated sepharose.

The lectin-Sepharose 4B complex is poured into a chromatographic column and washed free of any non-coupled lectin. A liquid containing sialoproteins or sialopeptides is run through the column. Sialoproteins and sialopeptides are bound by the lectin and retained in the column whereas other proteins or peptides wash through the column. The sialoproteins and sialopeptides can be recovered by washing the column with a liquid containing sialic acid and thus separated from the other components present in the original liquid. Furthermore, the sialoproteins can be fractionated by eluting them from the column with a buffer containing increasing concentrations of sialic acid, i.e., by gradient elution. The recovered sialoproteins can be further fractionated by any of several commonly used protein fractionating procedures such as: ion exchange chromatography, sieve chromatography, isoelectric focusing or chromofocusing or by sodium dodecyl sulfate polyacrylamide gel electrophoresis. This will permit a comparison of the sialopeptides or sialoproteins of biological fluid derived from the different individuals or sources.

The high degree of specificity of the slug lectin for sialic acid and sialoproteins enables the provision of a diagnostic method for quantitating the amount of sialic acid or sialoproteins in a biological liquid by determining its inhibitory effect on the agglutination of erythrocytes by the slug lectin. Thus, the method according to the present invention comprises contacting the said biological liquid with a predetermined quantity of the lectin described above and measuring the degree of hemagglutination effected by said lectin and comparing said measurement with the degree of hemagglutination effected by contacting an identical quantity of said lectin with a similar biological fluid containing a known amount of sialic acid or sialoprotein.

The degree of hemagglutination is preferably measured by determining the optical density at 620 nm of the lectin-treated biological liquid-erythrocyte suspension and comparing the optical density thereof with control samples containing a known sialopeptide or sialoprotein standard.

The present invention also provides a composition suitable for the diagnostic determination of the sialic acid content of the biological liquid of a mammal comprising an aqueous solution or suspension of an amount of the lectin described above sufficient to exert a measurable hemagglutinate effect on the biological liquid sample.

The aqueous solution or suspension preferably comprises isotonic saline and contains an amount of the slug-derived lectin sufficient to exert a measurable hemagglutinate effect.

The hemagglutinating activity of the slug lectin is highly specific for sialic acid. Of some 17 carbohydrates tested for their ability to inhibit hemagglutination by purified slug lectin, only N-acetylneuraminic acid and N-glycolylneuraminic acid were found to be effective. N-acetylneuraminic acid and N-glycolylneuraminic acid gave a 50% inhibition of hemagglutination at 0.13mM and 0.90mM, respectively. Further evidence for the sialic acid specificity of the slug lectin has been obtained by studies with the sialoproteins, fetuin and bovine submaxillary mucin (BSM). BSM at ~9 µg/ml and fetuin at ~50 µg/ml gave a 50% inhibition of the lectin hemagglutinating activity. Treatment of the sialoproteins with neuraminidase or 0.1N $H_2SO_4$ resulted in a loss of inhibitory activity which was proportional to the loss of sialic acid from these sialoproteins. Thus, the inhibition of slug lectin hemagglutinating activity by these sialoproteins appears to be due solely to their sialic acid residues.

The slug lectin is a relatively small molecule, consisting of two subunits of ~22,000 Daltons each, and is highly specific for sialic acid residues of sialoproteins. The lectin is particularly useful in the study of membrane structure and differences between normal and malignant cells as well as in the purification of sialoproteins and the comparison of the sialoprotein content of different biological fluids, such as serum, plasma, urine or tissue homogentates from normal and cancer patients.

EXAMPLES

Figure 1:
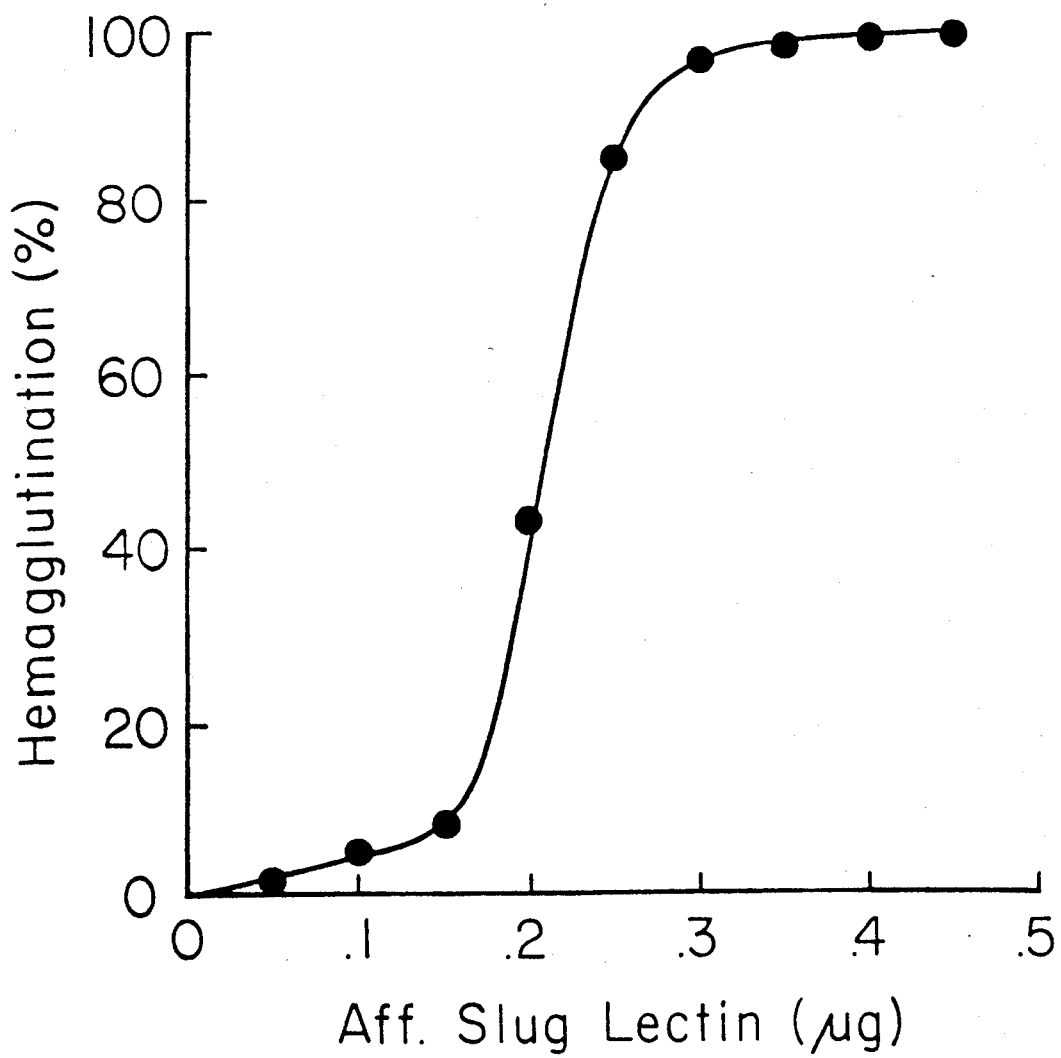
FIG. 1 is a plot showing the agglutination assay for the slug lectin.

Unless otherwise stated, all purification procedures were carried out at approximately 5° C.

Hemagglutination Assay: Aliquots of lectin were adjusted to 0.5 ml by addition of tris-saline buffer which contained 0.4 mg/ml gelatin. To this was added 0.5 ml of a solution containing human erythrocytes that had been washed several times with 0.9% NaCl and whose absorbance at 620 nm was ~2. After standing at room temperature for 30 min. the cells were gently pelleted by centrifugation in a Dynac centrifuge. The cells were resuspended by shaking and allowed to stand for 5 min. in order to permit aggregated cells to settle. The absorbance at 620 nm of the upper one-half ml of the erythrocyte suspension was measured and the data were plotted as $A_{620}$ versus $\mu g$ or $\mu l$ of lectin. One unit of activity is defined as the amount of LFA which gave a 50% agglutination. Percent agglutination was calculated as follows:

% Agglutination =

$$\frac{A_{620} \text{ of cell suspension} - (A_{620} \text{ of cell suspension} + \text{lectin})}{A_{620} \text{ of cell suspension.}} \times 100$$

Coupling of Bovine Submaxillary Mucin (BSM)[1] to 4B-Sepharose: Twenty ml of 4B-Sepharose were washed with 200 ml of deionized water by filtration, and the excess water was removed. The Sapharose was subsequently washed with 20 ml of 2M potassium phosphate (pH 12) by filtration and then placed in another ml of the phosphate buffer. Two and one-half ml of dioxane containing 1.0 g of cyanogen bromide were added over a 6 min. period while stirring the Sepharose in an ice bath. The Sepharose was stirred for an additional 10 min. and washed with 400 ml of deionized water. Ten ml of BSM (10 mg/ml) in 1.0M NaCl and 10 ml of 0.2M NaHCO$_3$, pH 9.0, were added to the activated Sepharose and the mixture stirred for 2 hr. at 22°. The BSM-Sepharose was washed with 100 ml of 1.0M NaCl and 100 ml of tris-saline buffer (0.05M tris-Cl-0.10M NaCl, pH 7.5 at 5° C.). The absorbance of the washes at 280 and 260 nm indicated that approximately 85% of the BSM had been coupled to the Sepharose.

Purification of Slug Lectin: Homogenates of whole slugs were highly viscous and were only partially clarified by centrifugation at 30,000×g for 30 min. Ammonium sulfate precipitates from such homogenates yielded highly viscous solutions when resuspended in buffer; the high viscosity of these solutions greatly hampered further purification of the LFA. The problems associated with highly viscous solutions can be eliminated by evisceration of slugs and use of only the body tissues for the lectin preparation. About 90% of the total agglutination activity was associated with the body tissues, about 5-7% was associated with the hemolymph and less than 2% was associated with the internal organs. Furthermore, most of the viscous material (presumably mucins) was associated with the viscera and thus was eliminated by this procedure.

Approximately 150 g of slugs were washed with deionized water, eviscerated, and further washed with tris-saline buffer to remove surface mucous material. One-hundred g of washed tissue were placed in 400 ml of tris-saline buffer containing 4.0 ml of phenylmethylsulfonyl-fluoride (5 mg/ml in 2-propanol). The tissue was minced with scissors and then homogenized by use of a polytron homogenizer at full speed for 3 min. The homogenate was centrifuged at 16,000×g for 15 min. And the supernatant fraction saved (SF-16). Powdered ammonium sulfate was added to the SF-16 to 40% saturation and the precipitate collected by centrifugation at 16,000×g for 15 min. The supernatant fraction was decanted and adjusted to 80% saturation by additions of powdered ammonium sulfate. The precipitate (AS-40-80) was collected by centrifugation at 16,000×g for 15 min. . The AS-40-80 pellets were resuspended in 200 ml of tris-saline buffer and dialyzed against three-one liter volumes of this buffer at 5° for 24 hrs.

A 1.6×10 cm column of BSM-Sepharose was equilibrated with tris-saline buffer. One-hundred ml of the dialyzed AS-40-80 fraction at approximately 10 mg of protein per ml were pumped (50 ml/hr) onto the column. The column was washed with tris-saline buffer until the non-bound proteins were eluted. The lectin was then eluted with tris-saline buffer containing 10mM AcNeu. The fractions containing protein which eluted with AcNeu were combined and dialyzed against tris-saline buffer before storage at −70°.

As indicated in Table 1, most of the agglutinin activity present in the tissue homogenate was recovered in the 40-80% ammonium sulfate fraction. Subsequent purification by affinity chromatography of LFA on BSM-Sepharose (FIG. 1) resulted in a 68-fold overall purification of LFA with a 22% recovery of agglutinin activity (Table 1). The use of BSM in conjunction with AcNeu as an agent in the affinity purification of LFA results in the recovery of a lectin which binds AcNeu. The low recovery (22%) and the apparently rather low degree of purification (68-fold) of LFA is probably due to a separation, at the affinity chromatography step, from other hemagglutinins which are specific for carbohydrate residues other than sialic acid, a suspicion confirmed by the data discussed below. In spite of the low recovery of hemagglutinin activity, approximately 17 mg of purified LFA was obtained from 100 g of eviscerated slug tissue.

TABLE I

Purification of a Sialic Acid Specific Slug Lectin[a]

| Fraction[b] | Volume (ml) | Protein (mg) | Specific Activity[c] (Units/mg protein) | Total Activity Units × 10$^{-3}$ | Recovery (%) |
|---|---|---|---|---|---|
| SF-16 | 434 | 5034 | 62 | 309 | 100 |
| AS-40-80 | 104 | 946 | 169 | 334 | 108 |
| Purified LFA | 28 | 16.8 | 4169 | 70 | 22 |

[a]One-hundred g of eviserated slug tissue were used in the preparation.
[b]The following notations are used: SF-16, the supernatant fraction obtained from a 16,000 × g centrifugation of the tissue homogenate; AS-40-80, proteins which precipitated between 40 and 80% saturation of SF-16 with ammonium sulfate; purified LFA, protein eluted from the BSM-Sepharose column with AcNeu, i.e., affinity purified LFA.
[c]One unit of activity is defined as that amount of lectin which gives a 50% agglutination of erythrocytes in the hemagglutination assay.

Removal of Bound AcNeu From Purified Lectin: Extensive dialysis of affinity purified lectin against tris-saline did not completely remove AcNeu. Assays of dialyzed lectin by the thiobarbituric acid assay of Warren, J. Biol. Chem., 234, 1971–1975 (1959) indicated that the lectin contained approximately eight moles of non-covalently bound AcNeu per mole of lectin. Chromatography of the lectin on a column (1×37 cm) of Dowex 501-X8(D) which had been equilibrated with 0.01M ammonium acetate, pH 7.0, reduced its AcNeu content to less than 0.20 moles of AcNeu per mole of lectin with little or no change in the specific activity of the lectin preparation. Because the yield of protein from such a treatment was ∼70% and because the removal of AcNeu had no effect on the lectin's specific activity, samples of lectin which had been chromatographed on the ion exchange column were utilized for only selected experiments.

Inhibition of Hemagglutination: An amount of purified LFA or partially purified LFA (i.e., AS-40-80 fraction) which gave greater than 95% agglutination of erythrocytes in the hemagglutination assay was mixed with varying amounts of potential inhibitors dissolved in tris-saline buffer, and the volume was adjusted to 0.5 ml by addition of tris-saline buffer. A 0.5 ml aliquot of erythrocytes was added to the lectin plus inhibitor solution and the percent agglutination determined as described above. The percent inhibition of agglutination represents the difference between the percent agglutination with lectin alone and that obtained with lectin plus inhibitor.

Chemical Analyses: Amino acid analyses of LFA were determined on a computerized Durrum 600 amino acid analyzer. Proteins samples were hydrolyzed at 110° in constant boiling HCl for 24, 48 and 72 hrs. Correction were made for loss of threonine and serine during hydrolysis. Cysteine was determined after performic acid oxidation of the protein. Tryptophan and tyrosine were estimated by the spectroscopic method of Edelhoch, Biochem., 6, 1948–1954 (1967) as modified by Bredderman, Anal. Biochem., 61, pp. 298–301 (1974). AcNeu was measured after acid hydrolysis of neuraminidase treatment of glycoproteins by the thiobarbituric acid assay described by Warren, supra. The acid hydrolytic release of AcNeu from glycoproteins was accomplished by incubation of the glycoprotein in 0.1N $H_2SO_4$ at 80° for 1 hr.

Physical Measurements: Sedimentation velocity and equilibrium measurements were performed in a Beckman model E analytical ultracentrifuge equipped with Schlieren/interference optics and a photoelectric scanner.

Sedimentation velocity measurements were made according to standard procedures; no corrections were made for the Johnson-Ogston effect. Meniscus depletion sedimentation equilibrium measurements employed the high speed or the long column methods. For all sedimentation equilibrium runs, attainment of equilibrium was checked by measuring the fringe displacements at several radial distances of two successive exposures taken 3 to 6 h apart. The partial specific volume used for LFA, as calculated from its amino acid composition, was 0.724 ml/mg. For LFA at pH 2, a correction was included for the Donnan effect on the equilibrium sedimentation pattern in a three-component system.

Empirical estimations of the hydrodynamic size of native LFA were attempted by gel chromatography on a 50 cm column of Bio-Gel P-200. Standard proteins of known hydrodynamic properties were utilized to calibrate elution positions from the column as a function of the equivalent hydrodynamic radius, or of the molecular weight. Empirical estimations of the size of the constituent polypeptide chains of LFA were by thin-slab sodium dodecyl sulfate ($NaDodSO_4$) polyacrylamide gel electrophoresis and by gel chromatography in the presence of 6M Gdm-Cl on Sephacryl S-300.

Circular dichroic spectra were measured on a Cary 60 spectropolarimeter equipped with a model 6002 CD attachment. The CD was calibrated with 10-d-camphorsulfonic acid. Cell path lengths from 0.5 to 10 mm were employed to maintain optimal signal to noise ratios. A value of 105 was used for the mean residue molecular weight. The differential refractometric method of Babul and Stellwagen, Anal. Biochem. 28, pp. 216–221 (1969) was employed to estimate protein concentration.

Absorption spectra were obtained on a Cary 15 spectrophotometer whose absorbance accuracies were checked with dichromate.

Figure 2:
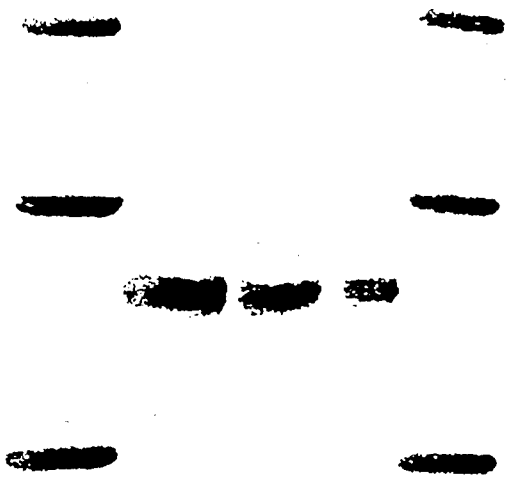
FIG. 2 is a sodium dodecyl sulfate polyacrylamide gel electrophoresis of the lectin.

Homogeneity of Purified LFA: Electrophoresis of the affinity purified LFA on $NaDodSO_4$-polyacrylamide gels (12.0%), after reduction and denaturation of the protein by $NaDodSO_4$ and $\beta$-mercaptoethanol, yielded a single Coomassie Blue staining band (FIG. 2). Electrophoresis was carried out on 1.5 mm slab gels by the reducing and denaturing method of Laemmli (1970). Lanes 1 and 5,5 µg each of myoglobin (17,200), chymotrypsinogen A (25,000), and ovalbumin (43,000); lane 2, 10 µg LFA; lane 3, 5 µg LFA; lane 4; 2.5 µg LFA. The migration of LFA relative to the migration of myoglobin, chymotrypsinogen A and ovalbumin suggests that reduced and denatured LFA consists of a single polypeptide species of molecular weight approximately 22,000. Some preparations of purified LFA exhibited a faster migrating minor component when a relatively large amount of LFA (>10 µg) was applied to the gel. Velocity sedimentation studies described herein below provide further evidence of homogeneity of the affinity purified LFA.

Figure 3:
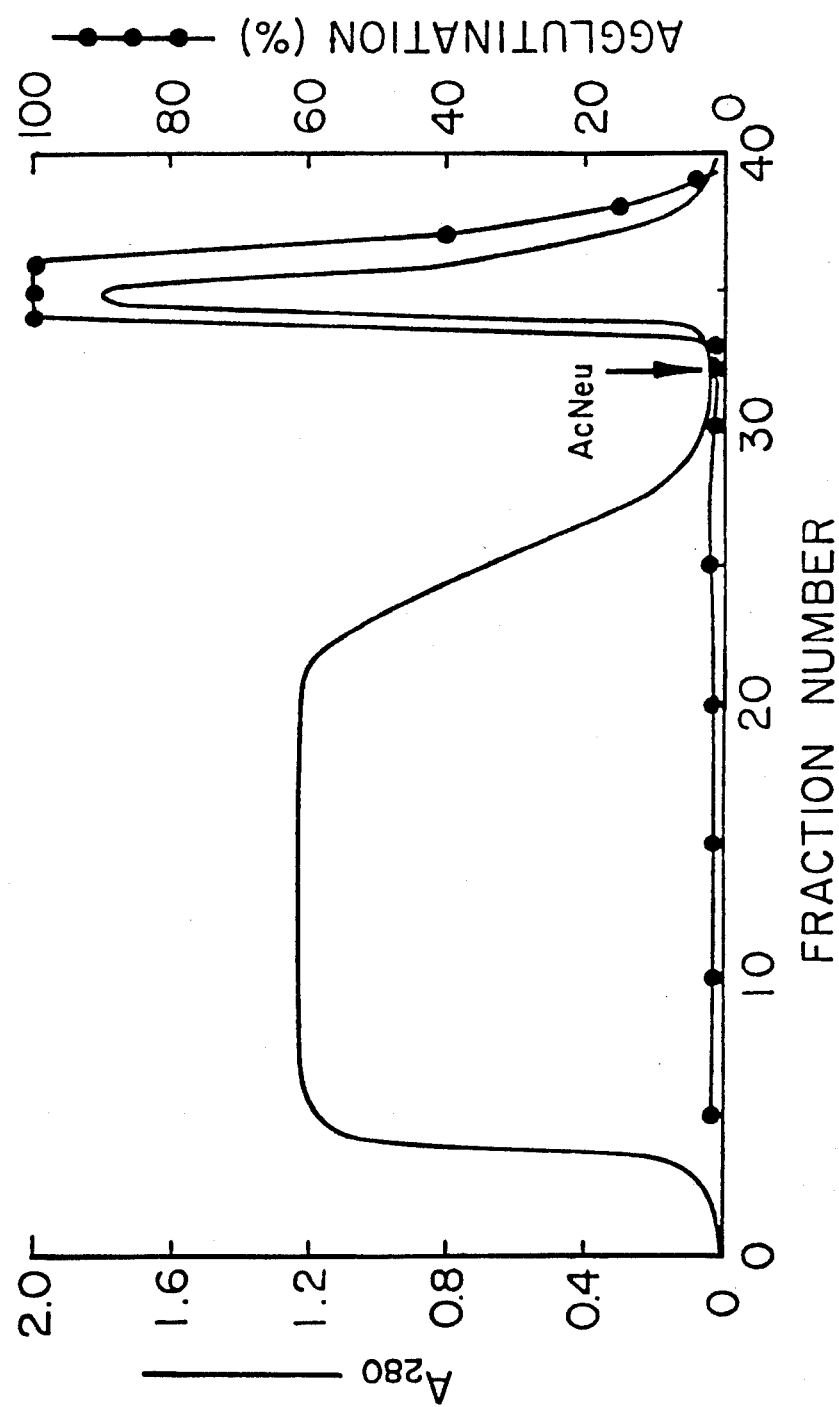
FIG. 3 is a plot of hemagglutinin activity against various fractions of protein.

Binding Properties of LFA: As indicated in Table II, hemagglutination by the affinity purified LFA was inhibited by 50% at 0.13mM and 0.81mM concentrations of AcNeu and GlyNeu, respectively. No inhibition was observed with the other carbohydrates tested, even at concentrations as high as 10–25mM. In contrast, inhibition of hemagglutination by the 40–80% ammonium sulfate fraction by GalNAc, GlcNAc, GalN and GlcN in addition to AcNeu and GlyNeu (Table II) suggests that this fraction contains hemagglutinins with binding specificities for carbohydrate residues other than sialic acid. Those fractions containing proteins which did not bind to the affinity matrix were without significant hemagglutinin activity (FIG. 3). Loss of agglutinin activity during the chromatography step may have been due to inactivation of lectins by denaturation or to loss of essential cations.

TABLE II

Inhibition of Hemagglutinin Activity of Slug Lectin by Carbohydrates[a].

| Carbohydrate | Carbohydrate Concentration (mM) | Inhibition (%) AS-40-80 Fraction | Inhibition (%) Purified LFA |
|---|---|---|---|
| N—Acetylneuraminic Acid | .05 | 6 | 1 |
| | .10 | 17 | 28 |
| | .15 | 27 | 54 |
| | .20 | 94 | 100 |
| N—Glycolyneuraminic Acid | .25 | 3 | 0 |
| | .50 | 20 | 2 |
| | .75 | 56 | 14 |
| | 1.0 | 88 | 85 |
| N—Acetyl-D-Galactosamine | 10.0 | 75 | 0 |
| N—Acetyl-D-Glucosamine | 10.0 | 53 | 0 |
| Galactosamine | 25.0 | 45 | 0 |
| Glucosamine | 25.0 | 19 | 0 |
| D(+)Galactose | 25.0 | 0 | 0 |
| D(−)Glucose | 25.0 | 0 | 0 |
| D(+)Mannose | 25.0 | 0 | 0 |
| α(+)Arabinose | 25.0 | 0 | 0 |
| D(+)Xylose | 25.0 | 0 | 0 |
| α-L(−)Fucose | 25.0 | 0 | 0 |
| D(−)Glucuronic Acid | 25.0 | 0 | 0 |
| α-Methyl-D-Glucoside | 25.0 | 0 | 0 |
| α-Methyl-D-Mannose | 25.0 | 0 | 0 |
| Lactose | 25.0 | 0 | 0 |
| Sucrose | 25.0 | 0 | 0 |

[a]The standard hemagglutination assay was used in these comparative studies. Twenty µg of protein from the 40–80% ammonium sulfate fraction (AS-40-80) or 0.34 µg of the purified LFA was utilized in each assay.

As mentioned above, the data of Table II shows that the purified LFA binds free AcNeu in a highly specific manner. This specificity was further tested by use of the AcNeu-rich glycoprotein, BSM. As shown in Table III, as little as 9 μg/ml of BSM gave a 50% inhibition of hemagglutination in the standard assay containing 0.34 μg of LFA. Upon treatment of BSM with *vibrio cholerae* neuraminidase, there was a time dependent release of AcNeu from the BSM with a concomitant loss in agglutination inhibition. The total content of AcNeu in BSM was 5% (w/w) as measured after its release by acid hydrolysis. Release of 12 μg of AcNeu per mg of BSM, i.e., 25% of its total AcNeu, virtually abolished its inhibitory activity. Thus, it appears that only about 25% of the AcNeu residues in BSM are the functional ligands in its interaction with LFA. This suggests that BSM may contain AcNeu residues that are inaccessible to LFA.

TABLE III

Inhibition of Hemagglutination by Neuraminidase Treated Bovine Submaxillary Mucin.

| | | μg BSM Required for 50% Inhibition | |
| --- | --- | --- | --- |
| Length of Incubation[a] (min.) | AcNeu Released[b] μg/μg BSM | BSM Incubation With Neuraminidase | BSM Incubation Without Neuraminidase[c] |
| 0 | 0 | 9 | 8 |
| 15 | 0.8 | 22 | 9 |
| 30 | 2.5 | 33 | 10 |
| 45 | 5.8 | 40 | 8 |
| 60 | 7.4 | 70 | 10 |
| 120 | 11.9 | >100 | 9 |

[a]A 1.0 mM solution of $CaCl_2$ containing 2 mg/ml BSM and 38 U of *Vibrio cholerae* neuraminidase was adjusted to pH 6.2 and incubated at 37°. Aliquots were removed at times indicated above, diluted 10-fold with .05 M tris-Cl-.1M NaCl, pH 7.5, and assayed with 0.34 μg slug lectin for inhibitory activity.
[b]Aliquots were assayed for released AcNeu by the thiobarbituric acid assay of Warren, supra.
[c]The BSM was incubated as described above except the neuraminidase was omitted from the incubation mixture.

Physico-Chemical Properties of LFA: The amino acid composition of LFA is summarized in Table IV. The lectin contains 40 residues of Glx plus Asx and a total of 32 residues of Lys, Arg and His per subunit. The high content of basic amino acids and the basic pI of the protein suggest that a relatively large proportion of the Glx and Asx are present in the protein in the amidated form.

TABLE IV

Amino Acid Composition of Slug Lectin.

| Amino Acid | Moles per 22,000 g[a] Nearest Integer |
| --- | --- |
| Asx | 26 |
| Thr | 13[b] |
| Ser | 13[b] |
| Glx | 14 |
| Pro | 4 |
| Gly | 22 |
| Ala | 16 |
| Val | 7 |
| Met | 2 |
| Ile | 7 |
| Leu | 15 |
| Tyr | 10 (9.6)[c] |
| Phe | 10 |
| His | 7 |
| Lys | 17 |
| Trp | (6)[c] |
| Arg | 8 |
| Cys | 6[d] |

[a]These values represent the average of values obtained from a 24, 48, and 72 hrs. hydrolysis in constant boiling HCl at 110°.
[b]Thr and Ser were corrected for losses during hydrolysis.
[c]The values in parentheses for Tyr and Trp were obtained by the spectroscopic method of Edelhoch, supra, as modified by Bredderman, supra.
[d]Cys (half-cystine) was determined by amino acid analysis after performic acid oxidation of the slug lectin.

Figure 4:
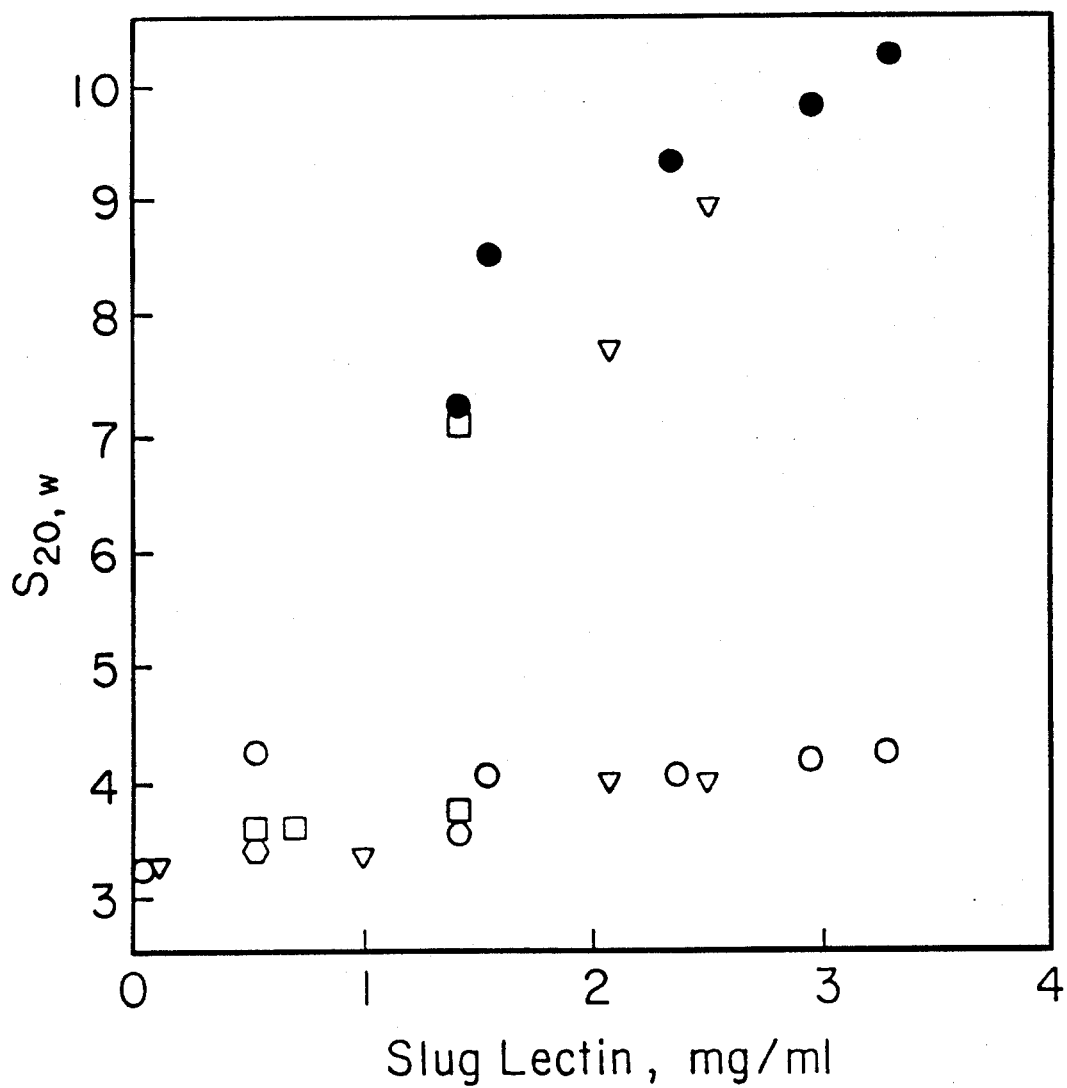
FIG. 4 is a plot of sedimentation velocity behavior of the lectin.

Although LFA exhibited a single electrophoretic component under dissociating and denaturing conditions (FIG. 2), appreciable size heterogeneity was evident during sedimentation velocity measurements at protein concentrations greater than 1 mg/ml. As illustrated by FIG. 4, these solutions exhibited two boundaries in the analytical ultracentrifuge. The magnitude of the sedimentation coefficient of the faster sedimenting species exhibited a marked positive dependence on the protein concentration to the point that at concentrations below 1 mg/ml only a single species of 3.4 S was observed. The 3.4 S species was present under all conditions and its sedimentation coefficient exhibited a slight positive concentration dependence. The relative ratios of the ultracentrifuge species could not be perturbed with AcNeu or chelating agents (FIG. 4). That these sedimentation velocity data are consistent with a rapidly associating-dissociating protein system is supported by the behavior of the near UV circular dichoism spectra of LFA at protein concentrations at or above which only the 3.4 S species could be observed in the analytical ultracentrifuge.

Figure 5A:
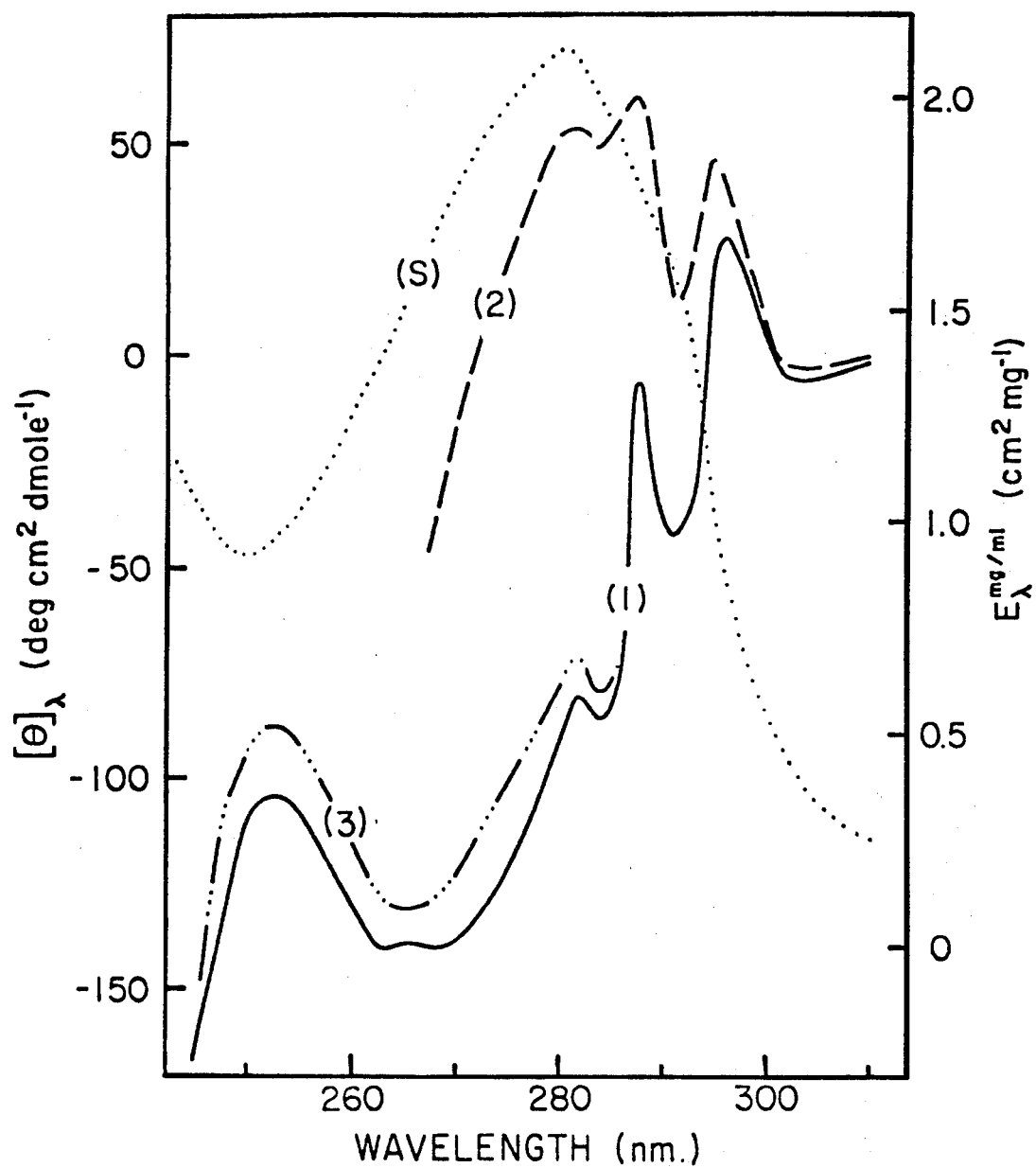
FIG. 5A is the circular dichroic and absorption spectra (near UV) of the lectin.
Figure 5B:
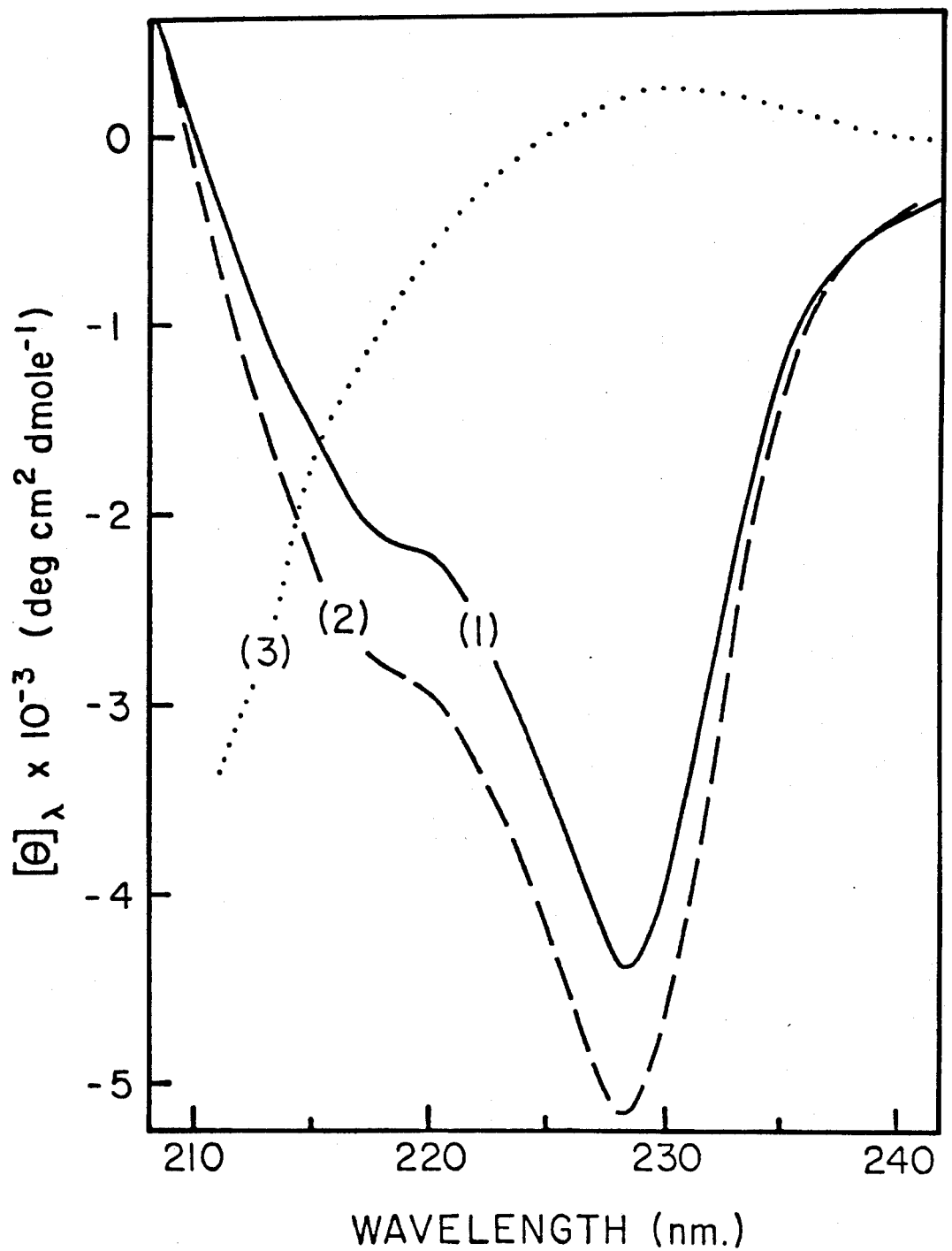
FIG. 5B is the circular dichroic and absorption spectra (for UV) of the lectin.

The amplitude of the ellipticity band at 282 nm increased with increasing protein concentration above ~0.6 mg/ml; this increase produced a marked qualitative change in the near UV spectrum (cf. curves 1 and 2 of FIG. 5A). Below ~0.6 mg/ml, the near UV spectra were qualitatively identical, but the amplitudes of the ellipticity bands fluctuated slightly among different preparations. In the absorbance range which could be measured at 280 nm (i.e. protein concentrations ≲1 mg/ml), LFA obeyed Beer's Law (absorption spectrum given in FIG. 5A). Thus, the near UV spectral data shows that the increased amplitudes of the near UV circular dichroism bands reflect an induced or enhanced chiral environment of one or more aromatic side chains upon association of lectin molecules. Slight increases in the ellipticity values were observed at all wavelengths in the far UV at protein concentrations above ~6.0 mg/ml (Curves 1 and 2 of FIG. 5B), but the magnitudes of these increases, up to ~13%, can be accounted for by the induced chirality of the aforementioned aromatic amino acid residues.

A cross-linked polyacrylamide gel chromatographic support medium was employed in an attempt to utilize it as a purification step and to estimate the equivalent hydrodynamic radius of native LFA. This type of support was employed rather than a gel of polysaccharide matrix to diminish the possibility of lectin-gel interactions. However, the elution position of LFA from the polyacrylamide gel was markedly dependent on the ionic strength of the eluting buffer: at 0.14 I, it eluted at a position equivalent to a protein of 15,000 MW, and at 1.04 I, it eluted at a position equivalent to a protein of 37,000 MW. This was apparently the result of ionic attractions between the basic protein and the support medium since a similar behavior was observed for chymotrypsinogen A, the only standard protein utilized with a P$^I$ similar to that of LFA.

Lines 1, 2 and 3 of Table V, summarize the results of the sedimentation equilibrium measurements on native LFA. Linear plots of ln (Fringe displacement) versus (radius)$^2$ were obtained from individual runs in dilute buffer at protein concentrations between 0.5 mg/ml and 0.05 mg/ml. When examine collectively, however, the weight-average molecular weights from these runs exhibited a tendency to increase slightly with increasing initial protein concentration. Neither the presence of a 30-fold molar excess of AcNeu (line 3) nor the complete absence of AcNeu (line 2) had an effect on the sedimentation equilibrium behavior of the protein. The native molecular weight estimated for LFA was 44,000±2,000. From this molecular weight, an s°$_{20,w}$ of 3.4 S, and a v of 0.724 mg/ml, the estimated f/f$_{min}$ of 1.35 suggests that LFA is a globular protein. A limited number of sedimentation equilibrium measurements at or below pH 3 suggest that like a number of other lectins the quaternary structure of LFA is disrupted at low pH (Table V, line 4).

The molecular weights of the constituent polypeptide chains of LFA were estimated by sedimentation equilibrium in 6M Gdm-Cl with and without reduction of disulfide bonds. In both cases (Table V, lines 7 and 8), the data were consistent with two polypeptide chains of the same molecular weight which are held together in the native molecule by noncovalent interactions. The circular dichroic spectrum of LFA in 6M Gdm-Cl (FIG. 4B, curve 3) supports the assumption that all noncovalent interactions in the protein were broken and that the minimal subunit had been obtained. These results are also supported by empirical molecular weight estimation methods in denaturing solvents (Table V, lines 9, 11). A comparison of the gel chromatographic behavior in 6M Gdm-Cl between reduced and unreduced LFA suggest that there is only limited restraint imposed on the polypeptide by intrachain disulfide bonds (Table VI, lines 9, 10). This observation is consistent with the half-cystine content of the protein (Table V) which suggests a maximum of only 1.5 disulfide bonds per 100 amino acid residues.

When LFA was exposed to a 40-fold molar excess of its receptor ligand, AcNeu, the only change observed in the circular dichroic spectrum of the protein was a diminution of about 10% in the amplitudes of the ellipticites between 240 and 285 nm (cf. curves 1 and 3 of FIG. 5A). Though this is a subtle change, it is consistent with previous observations on other lectins where the carbohydrate(s) for which the lectin is specific elicit a change in the near UV circular dichroic spectra. The far UV circular dichroic spectrum of LFA from which all free AcNeu had been removed exhibited no measurable change upon exposure of the lectin to a 40-fold molar excess of AcNeu.

TABLE V

| | Macromolecular Properties of Slug Lectin. | |
|---|---|---|
| | Physical Measurement | Magnitude |
| 1. | Molecular weight by sedimentation equilibrium, dilute buffer, pH 7.5; 4 concentrations, 3 rotor speeds | 44,000 ± 2,000 (6)$^a$ |
| 2. | Molecular weight by sedimentation equilibrium, AcNeu-free protein, dilute buffer 7.5 | 42,500 |
| 3. | Molecular weight by sedimentation equilibrium, dilute buffer plus 30 mM N—acetylneuraminic acid, pH 7.5; 3 concentrations | 43,800 (3) |
| 4. | Molecular weight by sedimentation equilibrium, dilute buffer plus 30 mM N—acetylneuraminic acid, pH 2.05 | 18,500$^b$ |
| 5. | s°$_{20,w}$ by sedimentation velocity, dilute buffer, pH 7.5 | 3.4 S ± 0.2 S |
| 6. | f/f$_{min}$ | 1.35 |
| 7. | Subunit molecular weight by sedimentation equilibrium, S—S reduced in 6 M Gdm.Cl | 22,000–26,000$^c$ (4) |
| 8. | Subunit molecular weight by sedimentation equilibrium, S—S unreduced in 6 M Gdm.Cl | 21,500–23,000$^c$ |
| 9. | Re by gel chromatography in 6 M Gdm.Cl, S—S reduced | 41.4 Å Mr = 19,100 |
| 10. | Re by gel chromatography in 6 M Gdm.Cl, S—S unreduced | 40.8 Å |
| 11. | Subunit molecular weight by NaDodSO$_4$ gel electrophoresis | 22,500 |
| 12. | E$_{280}^{mg/ml}$ | 2.1 ± 0.2 cm$^2$mg$^{-1}$ (3)$^a$ |
| 13. | v̄ from amino acid composition | 0.724 ml/g |
| 14. | pI from isoelectric focusing | 9–9.5 |

$^a$number of determinations
$^b$This includes a correction for the Donnan effect; a time-dependent decrease in M$_{app}$ was observed. This latter observation suggests an acid-catalyzed chain hydrolysis.
$^c$This range of values includes the precision of the ultracentrifuge data and the uncertainty of φ' in 6 M Gdm.Cl; values equal to, or 0.01 ml/g less than, v̄ were used for φ'.

The sialoproteins, bovine submaxillary mucin and bovin fetuin, are potent inhibitors of the slug lectin. Hemagglutination assays were performed as in FIG. 1 except that various amounts of the indicated protein in 0.5M tris-Cl-0.1M NaCl, pH 7.5 were added to the assay. The bovine submaxillary mucin preparation used contained only 5% N-acetylneuraminic acid as determined by the thiobarbituric acid assay of Warren (J. Biol. Chem., Vol. 234, pp. 1971–1975 (1959) and therefore was rather impure since the mucin has been reported to contain 36% N-acetylneuraminic acid (Gottschalk et al, "Glycoproteins", Elsevier Pub. Co., N.Y., p. 818 (1972)). However, the mucin preparation was a more potent inhibitor of the hemagglutinating activity of the slug lectin than was highly purified fetuin. (See FIG. 3). The bovin submaxillary mucin gave a 50% inhibition at 10 μg/ml and the fetuin gave a 50% inhibition at approximately 55 μg/ml. The increased inhibitory activity of the bovine submaxillary mucin may be due to impurities in the preparation or to an increased affinity of the slug lectin for the sialoglycopeptides found in the mucin. Asialylation of bovine submaxillary mucin and fetuin by incubation at 80° for one hour in 0.1N H$_2$SO$_4$ resulted in complete loss of inhibitory activity (FIG. 3). Furthermore, double diffusion of slug lectin in an agar gel against bovine submaxillary mucin or fetuin yielded precipitin lines which were lost when the mucin or fetuin were asialylated.

Coupling of Slug Lectin to Sepharose 4B: Five ml of affinity purified slug lectin at 1.0 mg/ml was dialyzed against 500 ml of 0.05M NaPO$_4$—0.1M NaCl, pH 6.8. The dialyzed slug lectin was coupled to 5 ml of Sepharose 4B by the cyanogen bromide activation procedure described previously for the coupling of BSM to Sepharose 4B.

Affinity Purification of Sialoproteins: The slug lectin-Sepharose 4B was poured into a one cm diameter column and washed with 0.05M Tris-Cl-0.10M NaCl, pH 7.5 to remove non-coupled slug lectin. An aliquot of serum or plasma (~0.14 ml) containing 10 mg of protein was diluted to 2.0 ml with the above tris-saline buffer and run onto the column of slug lectin-Sepharose 4B at a flow rate of ~0.5 ml/min. The column was washed with tris-saline buffer until non-bound proteins were eluted. Then sialoproteins were eluted by further washing the column with tris-saline containing 0.01M N-acetylneuraminic acid. Approximately 2.0 ml or 6 min. fractions were collected. Fractions containing non-bound proteins and fractions containing sialoproteins were combined separately.

Figure 6:
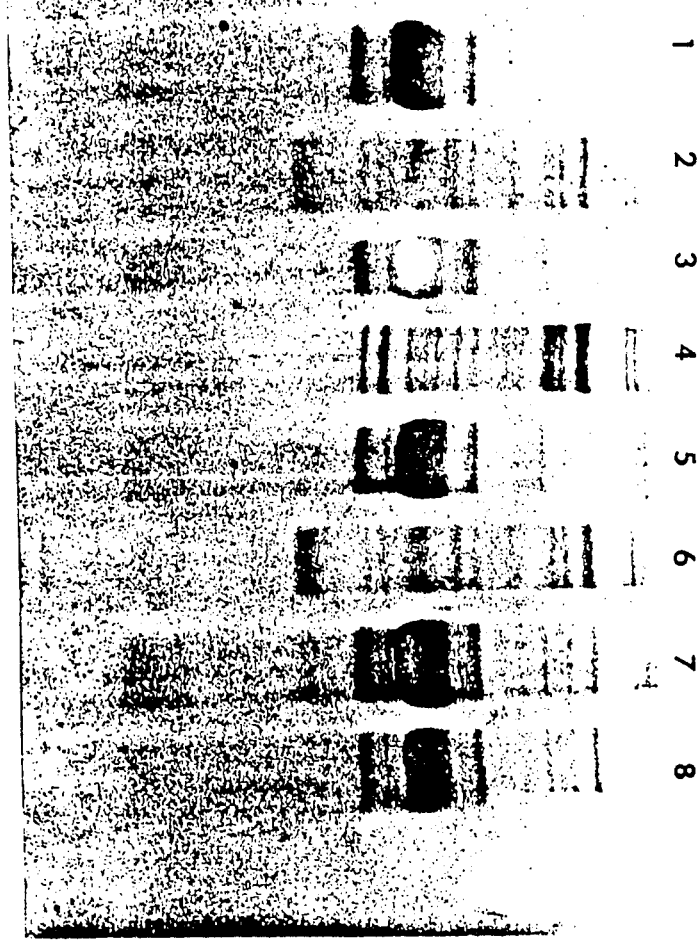
FIG. 6 is the sodium dodecyl sulfate polyacrylamide gel electrophoresis of lectin-sepharose affinity fractions from serum.

Separation of Sialoproteins by Sodium Dodecyl Sulfate-Polyacrylamide Gel Electrophoresis: An aliquot of the sialoproteins and non-sialoproteins, from the above affinity purification, containing 20 µg of protein was diluted to 0.27 ml with the tris-saline buffer. To this was added 0.03 ml of an 8-fold concentrated sample buffer (Laemmli, *Nature* (London), Vol. 227, pp. 680–685, (1970)) and the mixture was heated in a boiling water bath for 10 min. and then allowed to cool to room temperature. A 200 µl aliquot of the above solution was applied to a well in a 1.5 mm thick slab polyacrylamide gel and electrophoressed at 20 mA until the bromphenol blue had migrated to the bottom of the gel (~6 hr). The gel was removed, fixed in 40 ml of 12.5% trichloroacetic acid and 2.5 ml of a 0.25% aqueous solution of G250 Coomassie blue was added to the trichloroacetic acid to stain the sialoprotein bands. The stained gel was photographed, dried and stored. This provides a means of directly comparing the sialoproteins and/or sialopeptides present in the serum or plasma of various individuals (see FIG. 6). [Lanes 1,3, and 5, Non-bound or non-sialoproteins from serum samples. Lanes 2,4, and 6, Bound or sialoproteins from serum samples. Lanes 7 and 8, whole serum samples, i.e., non-fractionated]. The same procedure also provides a method for the separation and comparison of the sialoproteins or sialopeptides of other biological fluids such as urine or those solubilized from cellular membranes.

I claim:

1. A diagnostic method for determining the content of sialic acid or sialoprotein in a biological liquid comprising contacting the said biological liquid with a predetermined quantity of a substantially homogeneous lectin of the slug Limax flavus having a high degree of hemagglutinative inhibitory specificity and selectivity for sialic acid or sialoprotein having an approximate amino acid composition:

| Amino Acid | Moles per 22,000 g of Lectin (Nearest integer) |
|---|---|
| Asx | 26 |
| Thr | 13 |
| Ser | 13 |
| Glx | 14 |
| Pro | 4 |
| Gly | 22 |
| Ala | 16 |
| Val | 7 |
| Met | 2 |
| Ile | 7 |
| Leu | 15 |
| Tyr | 10 |
| Phe | 10 |
| His | 7 |
| Lys | 17 |
| Trp | 6 |
| Arg | 8 |
| Cys | 6 | and measuring the degree of hemagglutination effected by said lectin and comparing said measurement with the degree of hemagglutination effected with contacting an identical quantity of said lectin with a similar biological fluid containing a known amount of sialic acid or sialoprotein.

2. The diagnostic method of claim 1 wherein the degree of hemagglutination is measured by determining the optical density of the treated biological liquid.

3. The diagnostic method of claim 1 wherein said biological liquid is whole blood.

4. The diagnostic method of claim 1 wherein said biological liquid is plasma.

5. The diagnostic method of claim 1 wherein said biological liquid is serum or urine.

6. The diagnostic method of claim 1 wherein said liquid is tissue or cellular homogenate.

* * * * *